(12) United States Patent
Hsia et al.

(10) Patent No.: US 7,018,652 B2
(45) Date of Patent: *Mar. 28, 2006

(54) COMPOSITION AND METHOD FOR TREATING NONALCOHOLIC STEATOHEPATITIS

(75) Inventors: Houn Simon Hsia, Irvine, CA (US); David Fan, Newport Beach, CA (US)

(73) Assignee: Viva America Marketing, Inc., Costa Mesa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/714,127

(22) Filed: Nov. 13, 2003

(65) Prior Publication Data

US 2004/0105870 A1     Jun. 3, 2004

Related U.S. Application Data

(62) Division of application No. 09/726,688, filed on Nov. 29, 2000, now abandoned, which is a division of application No. 09/205,082, filed on Dec. 4, 1998, now Pat. No. 6,180,139.

(51) Int. Cl.
*A61K 9/20* (2006.01)
*A61K 9/14* (2006.01)
*A61K 31/685* (2006.01)
*A61K 31/355* (2006.01)

(52) U.S. Cl. ............... 424/464; 424/489; 424/702; 514/458; 514/474; 514/78; 514/725

(58) Field of Classification Search ............ 424/464, 424/489, 702; 514/458, 474, 78, 725, 811
See application file for complete search history.

(56) References Cited

U.S. PATENT DOCUMENTS

| 4,080,466 A | 3/1978 | Taninaka |
| 5,595,982 A | 1/1997 | Harless |
| 5,662,991 A | 9/1997 | Smolik et al. |
| 6,180,139 B1 | 1/2001 | Hsia et al. |

FOREIGN PATENT DOCUMENTS

WO     98/18491     5/1998

*Primary Examiner*—Gollamudi S. Kishore
(74) *Attorney, Agent, or Firm*—Orrick, Herrington & Sutcliffe LLP

(57) ABSTRACT

Nonalcoholic steatohepatitis (NASH) is a disease of the liver characterized by inflammation and damage to the liver cells. Typically, steatohepatitis involves inflammation of the liver related to fat accumulation, and mimics alcoholic hepatitis but is observed in patients who seldom or never consume alcohol. Nonalcoholic steatohepatitis can lead to serious liver damage, and ultimately cirrhosis. The present invention provides methods and compositions useful for the treatment or alleviation of nonalcoholic steatohepatitis and the pharmaceutical formulations for their administration to a human. Specifically, compositions comprised of lecithin, antioxidants and vitamin B complex are administered parenterally, most preferably by oral administration. Specific therapeutic formulations include admixtures of these compounds and specific dosage formulations include daily oral administrations of these compounds in tablet or powder forms.

13 Claims, No Drawings

COMPOSITION AND METHOD FOR TREATING NONALCOHOLIC STEATOHEPATITIS

CROSS REFERENCE TO RELATED APPLICATION

This is a divisional of co-pending application Ser. No. 09/726,688, filed on Nov. 29, 2000, which is a divisional of 09/205,082 filed on Dec. 4, 1998 U.S. Pat. No. 6,180,139 issued on Jan. 30, 2001.

The priority of the prior application is expressly claimed, and the disclosure of each of this prior application is hereby incorporated by reference in its entirety.

FIELD OF THE INVENTION

The present invention generally relates to dietary supplements containing lecithin, antioxidants and/or a vitamin B complex to treat liver disease. A preferred embodiment is a composition and the use thereof of a dietary supplement comprising lecithin, at least one antioxidant, and a vitamin B complex administered orally to treat or alleviate nonalcoholic steatohepatitis.

BACKGROUND OF THE INVENTION

The liver is the largest organ in the human body, located in the superior portion of the right upper abdomen. This organ is highly complex and specialized and performs many crucial biochemical functions. The liver is critically involved in the removal of toxins from the body and in the manufacture of proteins including energy storage and blood clotting factors. The liver is also involved in storing minerals, vitamins and glucose in the form of glycogen, which is metabolized in large quantities to provide energy. The liver also plays a role in red blood cell metabolism and the break-down of certain metabolic byproducts in the blood stream.

Nonalcoholic steatohepatitis (NASH) is a liver disease that is frequently reported in both men and women, although it most often appears in women and is especially prevalent in the obese. Although the disease has been observed to be accompanied by several other pathological conditions, including diabetes mellitus, hyperlipidemia and hyperglycemia, the cause and progression of the disease, as well as the causal or temporal relation to these conditions, is not well understood. However, in patients suffering from NASH, certain characteristics of liver tissue and abnormalities of function are typical. Specifically, fatty deposits, tissue degeneration, inflammation, cell degeneration, cirrhosis, elevation of free fatty acids and other such abnormalities have come to be associated with nonalcoholic steatohepatitis and are frequently seen in patients suffering from NASH.

Steatohepatitis, excess fat in the liver, is a condition often observed in cases of starvation, overloading of carbohydrates, absence of energy in the form of proteins, obesity, and cortico steroid therapy. It has been hypothesized that the accumulation of fat in the liver may be the result of increased accumulation of free-fatty acids, increased manufacture of fatty acids in the liver, decreased oxidation of free fatty acids, or the synthesis or secretion of LDL cholesterol. The increased level of free fatty acids in some cases of steatohepatitis may implicate the reactivity of free fatty acids with biological membranes. NASH patients exhibit increased asparate aminotransferase and/or alanine aminotransferase activity, characteristically at least 150% of normal. To confirm the clinical diagnosis of NASH, evidence of zero to low alcohol consumption is required and confirmation of the absence of a previous infection with hepatitis B virus or hepatitis C. The specific diagnosis of nonalcoholic steatohepatitis may also depend on detailed analysis of liver biopsy specimens. The histological features identified may include macrovesicular fat, cirrhosis, inflammation of the parenchyma and the presence of Mallory hyaline bodies.

Approximately 8% of patients who undergo liver biopsies will show histological evidence of NASH. The physiological condition that most commonly accompanies NASH is obesity, with approximately 70% and above of NASH sufferers also displaying clinically diagnosed obesity. NASH is particularly prevalent in obese patients who have undergone jejunal bypass to treat the obesity. In NASH patients, the extent of obesity tends to be generally correlated with the amount of steatosis and to be unrelated to non-insulin-dependent diabetes mellitus. However, non-insulin-dependent diabetes mellitis increases the prevalence of steatohepatitis especially in patients requiring insulin. Weight loss in patients before death does not appear to alleviate the steatosis and, somewhat paradoxically, obese patients who lost weight before death may actually have a higher incidence of steatohepatitis. The disease rarely occurs in any patient under the age of 30, but is particularly prevalent in patients in their 50s and 60s.

Even in NASH patients who do not consume any alcohol at all, liver biopsy specimens tend to mimic those seen in patients suffering from alcoholic hepatitis. However, a comparison of the two conditions reveals a higher incidence of vacuolation (indicative of diabetes) and steatosis in NASH as compared to alcoholic hepatitis. Patients suffering from alcoholic hepatitis also have a higher incidence of periportal and pericellular fibrosis and proliferation of the bioduct. Overall, the symptoms and histological damage observed in alcoholic hepatitis patients are more severe than in NASH.

Many experimental studies have been conducted to better understand NASH. For example, Susumu Itoh et al. studied 16 nonalcoholic steatohepatitis patients and 22 alcoholic hepatitis patients and discovered various differences between these two similar liver diseases. Susumu Itoh et al., *Comparison between Nonalcoholic Steatohepatitis and Alcoholic Hepatitis,* 82 The American Journal of Gastroenterology 650 (July 1987). Other examples include Ian R. Wanless & John S. Lentz, *Fatty Liver Hepatitis (Steatohepatitis) and Obesity: An Autopsy Study with Analysis of Risk Factors,* 12 Hepatology 5:1106 (1990)(concluding that fatty acids have a role in the hepatocellular necrosis found in some obese individuals) and Bruce R. Bacon et al., *Nonalcoholic Steatohepatitis: An Expanded Clinical Entity,* 107 Gastroenterology 1103 (1994)(concluding that NASH should not only be considered as a disease predominantly seen in obese women with diabetes).

Choline deficiency has been known to cause fatty infiltration of the liver in animals such as rats, hamsters, pigs and dogs. Thus, a deficiency in choline may result in the inability of the liver to transport fatty acids such as triglycerides. Indeed, one recent study has shown that hepatic steatosis in many long-term total parenteral nutrition patients may be caused by a deficiency in plasma-free choline, and that such deficiency may be reversed with lecithin (phosphatidylcholine) supplementation. Alan Buchman et al., *Lecithin Increases Plasma Free Choline and Decreases Hepatic Steatosis in Long-Term Total Parenteral Nutrition Patients,* 102 Gastroenterology 1363 (1992).

Although nonalcoholic steatohepatitis is generally viewed as a progressive liver disease, the condition tends to be stable over at least a few years in patients exhibiting the most common clinical manifestations of the disease. A majority of patients who have undergone repeated biopsies over a multi-year period have, for the most part, revealed no significant morphological changes over this period. To date, scientists have not discovered any biochemical, clinical or histological measurements that can distinguish between patients that will suffer comparatively stable NASH with those for whom NASH is a precursor to a more serious liver ailment, and even death.

Currently, an established therapy for patients suffering from NASH does not exist. Weight loss is a common prescription, simply because obesity is frequently found in patients suffering from NASH. The effect of a reduction in weight loss on NASH cannot be determined with certainty, however, because obese patients seldom maintain significant weight reduction.

SUMMARY OF THE INVENTION

The present invention is comprised of methods and compositions for the treatment or alleviation of nonalcoholic steatohepatitis, specifically, pharmaceutical formulations and methods for their administration to a human suffering from NASH as part of a treatment regimen to alleviate, or at least manage, the disease. Preferably, the composition is comprised of a dietary lecithin, antioxidant compounds, and/or B vitamin complexes. The pharmaceutical compositions are preferably formulated for oral administration in a dosage range that results in a decrease in hepatic steatosis indicated by increased liver density. In a preferred clinical application of the invention, a well-tolerated oral dosage is taken regularly by NASH patients whose liver function and histology is monitored for response to the formulation.

DETAILED DESCRIPTION OF THE INVENTION

The present invention is a pharmaceutically acceptable composition, usually administered as a dietary supplement, to treat or alleviate nonalcoholic steatohepatitis, with a principal aim to reduce hepatic steatosis. In a preferred embodiment, the composition comprises of a dietary lecithin supplement and a dietary supplement containing antioxidants and a vitamin B complex. The dietary lecithin supplement is preferably prepared in powder form. The antioxidant compounds and vitamin B complex may be combined into a single dosage and are preferably prepared together in tablet form. Preferably, a dosage in the range of 15 to 50 grams of the dietary lecithin supplement and 675 to 4050 milligrams (1 to 6 tablets) of the antioxidant/vitamin B complex supplement should be administered daily. Most preferably, however, 20 grams of the dietary lecithin supplement and 1350 milligrams (2 tablets) of the antioxidant/vitamin B complex supplement should be taken twice daily.

As used herein, the term "lecithin" includes choline and choline phospholipids such as phosphatidylcholine, and naturally occurring choline containing compounds in general, including derivatives of lecithin such as phosphatidylserine. "Lecithin" is primarily comprised of choline and inositol, two compounds that are used by the body in the break-down of cholesterol and dietary fats. Once lecithin is reduced to these two components, choline is converted into acetyl choline, a compound used in neurological activity including brain and muscle function. Lecithin may also function to help the body absorb Vitamin A, Vitamin D, and Thiamin in the digestive tract. Typically, dietary lecithin supplements contain lecithin/phosphatidylcholine/choline in a ratio of 1.1:10:50 and are sometimes ingested to reduce triglycerides and serum cholesterol. Additionally, lecithin has been investigated as an agent for the treatment of a wide variety of liver ailments, ranging from alcoholism to radiation exposure to exposure to toxic chemicals.

Phosphatidylserine is a phosphylipid that is implicated in the structural integrity and chemical function of cell membranes. Phosphatidylserine may also be taken as a supplement and is indicated in patients suffering from a deficiency of methyl donors, i.e., folic acid, Vitamin B12, and essential fatty acids that reduce the capacity of the brain to synthesize this compound.

Although, as noted above, dietary lecithin has been investigated as a remedy for certain liver ailments, sources of lecithin in the diet tend to be found in high-fat, high-cholesterol foods such as meat, liver and eggs which should be avoided by the typical NASH patient who tends to be obese. Therefore, pursuant to the present invention, dietary lecithin is preferably ingested orally as a supplement. The dietary lecithin supplement is available from commercial sources or may be manufactured by techniques known in the art. In the preferred embodiment, a granulated phospholipid fraction from soya lecithin enriched with phosphatidylcholine is used. This supplement comprises of phosphatidylcholine (minimum 50%), phosphatidylethanolamine (maximum 30%), lyso-phosphatidylcholine (maximum 5%), and other phospholipids (maximum 9%).

The "vitamin B complex" of the invention is a combination of two or more of the compounds that form the group of water soluble vitamins generally recognized as B vitamins, including vitamin B-1, B-2, B-3, B-5, B-6, B-7, B-12, and folic acid. As will be readily appreciated by those in the art, the invention also includes analogues, precursors, prodrugs and functional metabolic by-products of these compounds. In addition, these vitamins contained in natural extracts, yeast compounds, and concentrations of natural products may be administered pursuant to the invention.

Like all vitamins, B vitamins are essential to metabolism and other necessary biological functioning in higher organisms. As noted, B vitamins are water soluble and typically function as co-enzymes that interact with metabolic enzymes to complete certain, specific biochemical functions. Vitamin B-1, thiamine, functions to release energy from carbohydrates, alcohol, and fat. A biochemically active form of B-1, thiamine pyrophosphate, is a co-enzyme in certain metabolic processes including the citric acid cycle and the conversion of alanine to acetyl co-enzyme. Thiamine forms a co-enzyme following phosphorolation by ATP-dependent pyrophosphorylase. Thiamine pyrophosphate contains a substituted pyrimidine nitrogen heterocyclic ring and a thiazole nitrogen-sulfur heterocycle. The thiazole moitey provides the activity in the metabolism of pyruvate to provide a non-oxidative decarboxylation.

Vitamin B-2, riboflavin, is metabolized to form the flavin adenine dinucleotide (FAD) and flavin mononucleotide (FMN) co-enzymes. Both co-enzymes have an isoaloox-azine ring that accepts two electrons in enzymatic reactions. Biochemically, vitamin B-2 releases energy from protein, fats, and carbohydrates. Vitamin B-3, niacin or nicotinamide, is involved in the synthesis of pyridine nucleotides. Niacin reacts with adenosine to form nicotinamide adenine dinucleotide (NAD), which performs a critical function as an electron carrier in certain biochemical processes. Niacin is also reported to play an important role in digestive functions and in maintaining serum cholesterol levels. Biochemically, vitamin B-3 is involved in the oxidative metabolism of ingested food and appears to play a role in maintaining the circulatory system. Vitamin B-6, pyridoxine, is structurally similar to pyridine but features a hydroxymethyl group in the para position. Biochemically, the para-hydroxymethyl group is oxidized to form an aldehyde and the hydroxymethyl group in the meta position undergoes phosphorylation to yield a pyridoxal phosphate. Vitamin B-6 is metabolically involved in transaminations, decarboxylations, and chemical modifications to amino acids. Vitamin B-6 also appears to promote blood cell and hemoglobin formation and assists in carbohydrate protein and fat metabolism.

Vitamin B-12, cyanocobalamin, contains a monovilent cobalt metal centrally located in a porphyrin-like structure of tetrapyrrole rings. Biochemically, vitamin B-12 contributes a methyl group to the synthesis of certain compounds in numerous biochemical reactions, including specifically, a synthesis of choline and methionine. Vitamin B-9, folic acid, functions as a methyl donor following enzymatic reduction to tetrahydrofolate by reaction with the enzyme dihydrofolate reductase. Vitamin B-9 is reported to promote the formation of erythrocytes and to play a role in the maintenance of the neurological system.

The antioxidants of the present invention include at least one of vitamins C or E and preferably include other known antioxidants such as vitamin A and certain forms of selenium. Selenium is preferably administered in a selenium yeast composition that improves the bioavailability of the selenium. Such compositions are commercially available (Viva America Marketing, Inc., Costa Mesa, Calif.). As with the B vitamin complex, analogues, precursors, functional metabolics, concentrations of natural products and other substitutes for the isolated vitamin composition may be used. In the preferred embodiment of the invention, wherein the compositions are administered orally, the compositions may be administered in pill or liquid form. The pill form may be comprised of traditional pharmaceutically acceptable carriers and formulations such as preservatives, fillers, gums, stabilizers, and other functionally inert substances, such as sodium or calcium carbonate, calcium phosphate, lactose, and solidifying or binding agents such as gelatin, acacia, and pharmaceutically acceptable lubricants. A pharmaceutically acceptable formulation pursuant to the present invention meets the pharmaceutical industry standards for toxicity, mutagenicity, sterility, non-pyrogenicity, shelf-life stability, and overall standards of biocompatibility.

Pursuant to the present invention, antioxidants and a vitamin B complex are preferably administered together as part of a dietary supplement also containing lecithin. The contents of a suitable composition containing a combined antioxidant/vitamin B complex supplement are shown below in Table 1.

TABLE 1

| Description | Unit (mg) per tablet |
| --- | --- |
| Thiamine Mononitrate (Vitamin B-1) | 1.500 |
| Riboflavin (Vitamin B-2) | 1.753 |
| Niacinamide (Vitamin B-3) | 20.101 |
| Pyridoxine HCL (Vitamin B-6) | 2.062 |
| Cyanocobalamin (Vitamin B-12) | 0.600 |
| D-Calcium Pantothenate | 10.870 |
| Folic Acid (Vitamin B-9) | 0.408 |
| D-Biotin (Vitamin H) | 30.000 |
| Barley Juice Powder | 215.154 |
| Wheat Spout Powder | 100.000 |

TABLE 1-continued

| Description | Unit (mg) per tablet |
| --- | --- |
| Beta Carotene | 5.000 |
| Ascorbic Acid | 50.000 |
| Vitamin E Acetate | 71.429 |
| Selenium Yeast 1,600 MCG/GM | 15.625 |
| Stearic Acid Powder | 3.250 |
| Sylox (Silicon dioxide) | 9.750 |
| Magnesium Stearate | 6.500 |
| MCC (Methyl crystalline cellulose) | 131.202 |
| Total | 675.200 |

All of the other components of the antioxidant/vitamin B complex compositions are available from commercial sources.

Having generally described the present invention, a further understanding may be acquired by reference to the following Example, an experimental study conducted to investigate the effects of dietary supplementation with lecithin, antioxidants and a vitamin B complex in NASH patients.

EXAMPLE I

Four patients, one male and three female, were recruited who had increased aspartate aminotransferase (AST) and/or alanine aminotransferase (ALT), at least one and a half times the upper limits of normal, and a liver biopsy which demonstrated NASH within three months prior to entering the study. These patients did not have other chronic liver disease, and were not on total parenteral nutrition or lipid lowering agents. Each patient was given 20 grams of dietary lecithin supplement with antioxidants (vitamins A, C, and E and selenium) and vitamin B complex 300 percent of the RDA daily level twice a day for a total of 12 weeks.

Serum levels of AST, ALT, GGT (gamma-glutamyltranspeptidase), alkaline phospatase, total bilirubin, lipid profile, free choline and phospholipid bound choline of plasma and red blood cell were measured at entry, week 4, week 8, and week 12. A computed tomography (CT) scan of liver was obtained at entry and week 12. Another liver biopsy was performed after the treatment to confirm the change of fatty infiltration measured by the CT scan. Portal inflammation, lobular activity, steatosis, and fibrosis were graded from 0 to 4. The Average CT tissue density in Hounsfield Units (HU) for liver and spleen was generated from multiple representative sections. Liver density was determined by the liver-spleen differential, with 0 to 8 HU representing borderline fatty changes and negative HU values corresponding to marked fatty infiltration.

The study was completed by all four patients without adverse drug reaction. Furthermore, all four patients showed a statistically significant decrease in hepatic steatosis indicated by increased liver density as measured by CT scans (4.97±4.65 HU before treatment vs. −5.21±8.07 HU after treatment; $p<0.05$). On histology, two out of four patients had a reduction in steatosis. No change in portal inflammation was observed, however, two out of four patients had mildly increased lobular activity. Although a small increase in fibrosis was observed, it cannot be concluded whether this is a positive or negative effect. Increased fibrosis may result from focal sampling bias, moreover, fibrosis has been observed to correlate with a degree of obesity and the existence or development of fibrosis is not known to be directly correlated with the development or progression of NASH. Detailed biopsy results are shown below in TABLE 2.

TABLE 2

| Patent Number | | Portal Inflammation | Lobular Activity | Steatosis | Fibrosis | Iron | Glycogenated Nuclei |
|---|---|---|---|---|---|---|---|
| #1 | Pre-treatment | 1 | 0 | 2 | 2 | 1 | 1 |
|  | Post-treatment | 1 | 1 | 1 | 3 | 1 | 1 |
| #2 | Pre-treatment | 2 | 1 | 2 | 2 | 0 | 0 |
|  | Post-treatment | 2 | 2 | 1 | 2 | 0 | 0 |
| #3 | Pre-treatment | 0 | 2 | 3 | 0 | 0 | 0 |
|  | Post-treatment | 0 | 2 | 3 | 2 | 0 | 0 |
| #4 | Pre-treatment | 0 | 1 | 1 | 0 | 0 | 1 |
|  | Post-treatment | 0 | 1 | 1 | 1 | 0 | 0 |

There will be various modifications, improvements, and applications of the disclosed invention that will be apparent to those of skill in the art, and the present application encompasses such embodiments to the extent allowed by law. Although the present invention has been described in the context of certain preferred embodiments, the full scope of the invention is not so limited, but is in accord with the scope of the following claims.

The invention claimed is:

1. A method for the treatment of nonalcoholic steatohepatitis comprising:
   administering a pharmaceutically acceptable formulation for oral administration to a human in need thereof wherein the formulation is comprised of:
   one or more vitamin B complex vitamins, and
   an antioxidant.

2. The method of claim 1 wherein the lecithin is the form of is comprised of a granulated phospholipid fraction of soya lecithin containing at least 50% phosphatidylcholine, at least 5% lysophosphatidylcholine and no more than 30% phosphatidylethanolamine.

3. The method of claim 1 wherein the one or more vitamin B complex vitamins are selected from the group consisting of vitamin B-1, vitamin B-2, vitamin B-3, vitamin B-5, vitamin B-6, vitamin B-7, and vitamin B-12 and combinations thereof.

4. The method of claim 1 wherein the antioxidant is comprised of vitamin C.

5. The method of claim 1 wherein the antioxidant is comprised of vitamin E.

6. The method claim 1 wherein the antioxidant is a bioavailable selenium.

7. The method of claim 1 wherein the step of administering the formulation for oral administration is comprised of administering between approximately 15 to 50 grams.

8. The method of claim 1 wherein the dosage of the combination of the antioxidant and the B vitamin complex is between approximately 675 to 4050 milligrams.

9. The method of claim 1 wherein the formulation for oral administration is prepared as a daily dosage of approximately 20 grams of lecithin and 1350 milligrams of the comination of antioxidants and B complex vitamins .

10. The method of claim 1 wherein the formulation further vitamins is vitamin A.

11. The method of claim 1 wherein one or more B comlex comprises folic acid.

12. The method of claim 1 wherein the pharmaceutically acceptable formulation for oral administration comprises a pill.

13. The method of claim 1 wherein the pharmaceutically acceptable formulation for oral administration comprises a liquid.

* * * * *